United States Patent [19]

Mitchnick et al.

[11] Patent Number: 5,536,492
[45] Date of Patent: Jul. 16, 1996

[54] COSMETIC COMPOSITIONS CONTAINING HYDROPHOBIZED ZINC OXIDE

[75] Inventors: Mark Mitchnick, East Hampton, N.Y.; Anthony J. O'Lenick, Jr., Lilburn, Ga.

[73] Assignees: Siltech Inc., Norcross, Ga.; SunSmart Inc., Wainscott, N.Y.

[21] Appl. No.: 549,873

[22] Filed: Oct. 30, 1995

Related U.S. Application Data

[63] Continuation-in-part of Ser. No. 490,494, Jun. 14, 1995, Pat. No. 5,486,631.
[51] Int. Cl.⁶ .................................................. A61K 7/42
[52] U.S. Cl. ................................................... 424/59
[58] Field of Search .................................................. 424/59

[56] References Cited

U.S. PATENT DOCUMENTS

| | | | |
|---|---|---|---|
| 5,380,527 | 1/1995 | Legrow et al. | 424/59 X |
| 5,441,726 | 8/1995 | Mitchnick et al. | 44/59 |
| 5,447,715 | 9/1995 | Roberts | 424/59 |
| 5,476,643 | 12/1995 | Fogel | 424/59 X |

*Primary Examiner*—Paul F. Shaver

[57] ABSTRACT

A process for protecting the skin from ultra violet rays of the sun which comprises contacting the skin with an effective protecting concentration of a hydrophobized zinc oxide, is disclosed. The zinc oxide is hydrophobic, non-reactive, and not affected by water.

20 Claims, No Drawings

COSMETIC COMPOSITIONS CONTAINING HYDROPHOBIZED ZINC OXIDE

RELATED APPLICATIONS

This application is a continuation in part of Ser. No. 490,494, filed Jun. 14, 1995, now U.S. Pat. No. 5,486,631.

This invention relates to the use of a silicone composition, containing a hydrophobized zinc oxide in a process of protecting the skin from ultra violet rays.

The process involves the utilization of a specific type of hydrophobized zinc oxide, which is very water insoluble and very inert to reaction. This type of zinc oxide is very effective in providing a treatment to the skin which does not wash off with water and which provides ultra violet protection which is both better than that which is achieved with untreated zinc oxide, both initially and more importantly with time.

DESCRIPTION OF THE ART

Zinc oxide is a well known material useful in a variety of applications. It is used as a pigment in paint, as an additive in cosmetic products, cements, glass, rubber, glue, matches, inks and semiconductors. The use of zinc oxide in so many applications areas is a direct result of the many differing properties of the pigment.

Zinc oxide is a reactive material which exhibits a wide range of reactivity with alkaline as well as acidic solutions, liquids and gases. In some applications the reactive nature of the zinc oxide is desirable, for example in paint applications, the reactivity of the pigment results in adhesion into the polymer film. In many applications, it is highly desirable to have zinc oxide in a non-reactive form, that is to eliminate, or make unavailable, the active sites present on the molecule.

Harvey Brown in his book Zinc Oxide Properties and Applications (International Lad Zinc Research Organization) states zinc oxide displays a high degree of reactivity in water with a wide range of materials, including acids, acid salts, and alkaline materials. Many of the resulting compounds are complex structures because of the variety of species furnished by zinc oxide in aqueous solution. Brown goes on to state that zinc oxychloride, zinc phosphates, zinc silicates, and a variety of other materials can be formed in aqueous media. One measure of the availability of reactive groups on the zinc oxide is pH change associated with use of zinc oxide. Zinc oxide containing reactive sites can increase the pH of aqueous products. In some instances the increase can be from an initial pH of 7 to a pH of 8.7. This increase is not only a measure of the presence of reactive groups, but is highly undesirable in the formulation.

It is therefore very desirable to produce a zinc oxide which has the pigment properties but lacks the reactivity found in untreated zinc oxide.

One area in which zinc oxide has been used is in sun screen products. It protects the skin from sun. The traditional materials used for protecting the skin from the harmful effect of the sun are the organic sun screens. These include para amino benzoic acid and other materials which absorb ultra violet light. Recently, studies have indicated that ultra violet light is a major factor in the ageing of skin.

This has resulted in the incorporation of sun screens in products which are not aimed specifically for use at the beach, like make up. Additionally, there has been an increased interest in providing higher levels of protection to the skin. The so called SPF system has been developed to evaluate various materials for their effectiveness in protecting the skin from the damaging affects of the sun. The quest for higher and higher SPF values has resulted in the use of greater levels of organic sun screen. These materials have a tendency to be irritating at high concentrations, and have the affect of increasing the available organic material for bacteria. This results in the need for more preservative to protect the higher level of organic sun screen agent from bacterial degradation. The higher levels of preservative result in higher irritation levels, which can be addressed by incorporation of irritation mitigants, which themselves are degraded by bacteria.

The use of inorganic sun screen agents like zinc oxide is a good way around the use of organic sun screens, since they are not attacked by bacteria. However, their use does have some other inherent problems. Specifically, these materials are not easily formulated into stable products, due to the reactivity issues raised above. Zinc oxide tends to agglomerate in many finished formulations, loosing it's effectiveness in the formulation and resulting in unacceptable aesthetic results, most commonly whitening and viscosity changes. Additionally, zinc oxide tends to raise the pH of the formulation to about 8.5 which is too high for many skin care formulations. These formulations tend to be useful at a pH of 6–7. Zinc oxide has limited usefulness as is due to these problems.

One approach has been to pre-disperse the zinc oxide in an organic oil like Siltech's patented tri-(octyldodecyl)citrate. While the dispersion is fairly stable, the coating is not permanent since there is no reaction between the oil and the zinc oxide. The oil also disrupts the uniformity of the zinc oxide on the skin. Traditionally, dispersing aids have been added to formulations to minimize the disruptive effect upon the film. These include phosphate esters, and lecithin. These too suffer from the labile nature of the surface treatment and dissociation between the particle and the oil. This is especially evident when zinc oxide is exposed to extreme mechanical or thermal stress as in the production of plastics or stick cosmetics.

The present invention overcomes the shortfalls of zinc oxide by reacting a specific silicone compound under controlled conditions to produce a stable, surface treated zinc oxide which maintains it's state of dispersion and does not contribute significantly to chemical instability in the formulation. The contacting of the skin with an effective skin protecting concentration of the treated zinc oxide results in both initial and long term sun protection heretofore unattainable.

SUMMARY OF THE INVENTION

The present invention discloses a process for protecting the skin from the sun's ultra violet rays by contacting the skin with an effective protecting concentration of a specific hydrophobized zinc oxide. The parent application covers the composition and process for preparing the hydrophobic zinc oxide, this application is directed to novel compositions using the hydrophobized silicone.

DETAILED DESCRIPTION OF THE INVENTION

We have found a process for protecting the skin from the ultra violet rays of the sun, which comprises contacting the skin with an effective protecting concentration of a hydrophobic zinc oxide which is prepared by the reaction of a silicone compound conforming to the following structure:

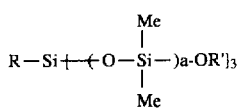

Me is methyl;

R is alkyl having one to ten carbon atoms;

R' is methyl or ethyl;

a is an integer ranging from 4 to 12;

with zinc oxide.

We have surprisingly learned that the value of "a" is critical in developing a product which gives the desired hydrophobicity. The critical range is from 4 to 12. Zinc oxide's value as a pigment is based upon it's ability to remain dispersed and unreacted. Untreated zinc oxide, placed into water, loses its effectiveness and good aesthetic qualities due to agglomeration. If the value of "a" is too low, the treated zinc oxide is not sufficiently hydrophobic and it's value as a pigment is destroyed. Making zinc oxide permanently hydrophobic by treatment with the correct silicone compound is highly desirable and heretofore very difficult to attain.

The compounds of the present invention are hydrophobic zinc oxide which is prepared by the reaction of a silicone compound conforming to the following structure:

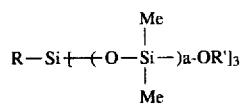

Me is methyl;

R is alkyl having one to ten carbon atoms;

R' is methyl or ethyl;

a is an integer ranging from 4 to 12;

reacted with zinc oxide.

The zinc hydrophobizing process comprises; contacting zinc oxide with an effective hydrophobizing concentration of a silicone which conforms to the following structure:

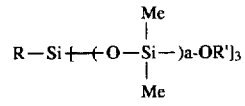

Me is methyl;

R is alkyl having one to ten carbon atoms;

R' is methyl or ethyl;

a is an integer ranging from 4 to 12;

then heating the mixture to a temperature of between 40° C. and 100° C., for two to ten hours.

The product so produced surprisingly is hydrophobic and maintains the desirable performance characteristics making the zinc oxide useful in many applications including as a sun screen.

While not wishing to be limited to a specific theory of why only specific silicone compounds of the present invention are effective, we believe that the placement of the reactive groups on the molecule have a dramatic affect upon the efficiency of hydrophobization.

The reaction by which hydrophobization occurs is one in which active sites on the zinc oxide reacts with the silicone to result in a covalent bond between silicone and zinc oxide, and the formation of R'OH. The reaction is summarized as follows:

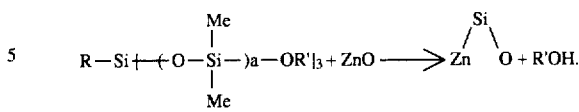

It should be clear from the above that the presence of three R' groups on the silicone compound can result in the formation of a multiple bonds bond between silicone the zinc oxide crystals. Since no water is present in this process, the zinc oxide crystals remain intact and "frozen" in shape by the silicone which acts like a matrix for the zinc oxide crystals. The silicone preserves the structure of the zinc oxide crystals, eliminates the reactivity in water, and makes them hydrophobic. This allows for the exposure of the hydrophobic zinc oxide to water without deleterious affect to the zinc oxide or pH drift caused by the reactivity of the zinc oxide in aqueous products. All these improvements are a direct unexpected result of modifying the surface of the zinc oxide with a specific silicone compound, freezing the structure of the zinc oxide, hydrophobizing it and removing the undesired reactivity.

When drawn out in it's full structure, it becomes clear that the position of the R' groups can be varied by variation in "a". That is as "a" increases the distance between the R' groups increase and the three dimensional structure changes.

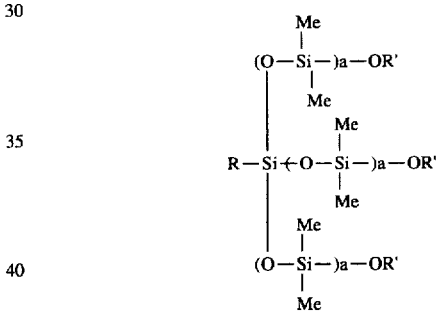

We have learned that the value of "a" is critical to the functionality of the hydrophobizing process. Specifically, "a" is zero, the treated zinc oxide does not maintain it's structure when exposed to water. There is little affect upon the effectiveness of the hydrophobization until a value of about 4 is reached. The best performance is attained as a approaches 8. As "a" is increased further the silicone molecule becomes more hydrophobic and higher in molecular weight, this limits it's effectiveness in coating the zinc oxide. In effect the reactive silicone is acting more like an oil than like a hydrophobizing agent, resulting in a zinc oxide which is not covalently bonded to silicone. A non covalent bond is easily removed by contact with water, resulting in agglomeration of the zinc oxide, an elevation of the pH of the formulation, due to reactive groups present in the zinc oxide, and silicone oil floating on the top of the aqueous formulation.

The production of R'OH as a by product in a dry process, as opposed to s slurry process, is very desirable. Another approach is the use of silicone compounds containing silanic hydrogen compounds of the structure Si—H, results in the evolution of copious amounts of flammable hydrogen gas. In addition the use of these kinds of compounds do not give the desired properties.

PREFERRED EMBODIMENTS

In a preferred embodiment the process has an effective protecting concentration ranges between 0.1% and 25% by weight. The reminder can be made up of water, mineral oils, esters or combinations thereof.

In another preferred embodiment the effective protecting concentration ranges from 0.5% and 20% by weight hydrophobic zinc oxide.

In still another preferred embodiment the effective protecting concentration ranges from 1.0% and 10% by weight hydrophobic zinc oxide.

In a preferred embodiment a is an integer ranging from 6 to 12.

In another preferred embodiment a is an integer ranging from 4 to 8.

In another preferred embodiment R is methyl.

In another preferred embodiment R is octyl.

In another preferred embodiment R is isobutyl.

In another preferred embodiment R is ethyl.

EXAMPLES

Silicone Compounds

The silicone compounds useful for the preparation of the compounds of the present invention were provided by Siltech Inc. and conform to the following structures:

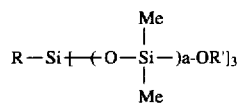

Me is methyl;

R is alkyl having one to ten carbon atoms;

R' is methyl or ethyl;

a is an integer ranging from 4 to 12.

Silicone Compounds Useful for the Present Invention

The following are examples of materials which are compounds useful in treating the zinc oxide according to our invention;

| Silicone Example | R | R' | a |
|---|---|---|---|
| 1 | $CH_3$ | $CH_3$ | 4 |
| 2 | $CH_3$ | $CH_2CH_3$ | 8 |
| 3 | $CH_3$ | $CH_3$ | 12 |
| 4 | $C_4H_9$ | $CH_3$ | 4 |
| 5 | $C_4H_9$ | $CH_2CH_3$ | 12 |
| 6 | $C_8H_{17}$ | $CH_3$ | 4 |
| 7 | $C_8H_{17}$ | $CH_2CH_3$ | 8 |

Silicone Compounds Not Useful for the Present Invention (For comparison)

| Silicone Example | R | R' | a |
|---|---|---|---|
| 8 | $CH_3$ | $CH_3$ | 0 |
| 9 | $CH_3$ | $CH_2CH_3$ | 2 |
| 10 | $C_4H_9$ | $CH_3$ | 0 |
| 11 | $C_4H_9$ | $CH_2CH_3$ | 2 |

Zinc Oxide

Zinc Oxide used in the preparation of the compounds of the present invention are commercially available from, Zinc Corporation of America, and Sun Smart Inc. The zinc oxide can be of many shapes or combinations of shapes including spherical, rod, needle flat etc.

The zinc oxide used in the preparation of the products in the examples are SunSmart's.

Process

The compounds of the present invention are prepared by contacting zinc oxide with an effective hydrophobizing concentration (generally between 0.1% and 25% by weight of the total formulation) of a silicone which conforms to the following structure:

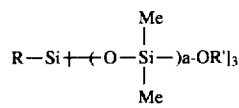

Me is methyl;

R is alkyl having one to ten carbon atoms;

R' is methyl or ethyl;

a is an integer ranging from 4 to 12;

then heating the intermediate to a temperature of between 40 C. and 100 C., for between 2 hr and 10 hr. During this time alcohol is removed. The reaction is considered complete when 97% of the theoretical alcohol is removed. The quantity of alcohol removed is considered more important than the time at which the material is held at temperature.

When R' is CH3, the alcohol removed is methanol. When R' is CH2CH3 the alcohol removed is ethanol.

The zinc oxide is coated dry. The silicone can be applied by simply mixing it with the zinc oxide, or in a preferred method using traditional methods for applying liquids to solids like a "V" blender.

Example 12

To 90.0 grams of zinc oxide is added 10.0 grams of silicone Example #1. The powder is then mixed well. The powder is then placed in an oven and heated to 80 C., for 6 hr. During this time alcohol is removed. The reaction is considered complete when 97% of the theoretical alcohol is removed. The amount of alcohol removed is determined by weighing the container.

Examples 13–22

Example 12 is repeated only this time the specified amount of the specified silicone is added in place of the 10 grams of silicone Example 1 and the specified number of grams of zinc oxide are used.

Compounds of the Present Invention

| Example | Silicone Compound Example/Grams | Zinc Oxide Grams |
| --- | --- | --- |
| 13 | 2 | 25.0 | 75.0 |
| 14 | 3 | 1.0 | 99.0 |
| 15 | 4 | 5.0 | 95.0 |
| 16 | 5 | 10.0 | 90.0 |
| 17 | 6 | 0.1 | 99.1 |
| 18 | 7 | 10.0 | 90.0 |
| 19 | 8 | 25.0 | 75.0 |
| 20 | 9 | 1.0 | 99.0 |
| 21 | 10 | 5.0 | 95.0 |
| 22 | 11 | 10.0 | 90.0 |

Applications Results (a) Particle Size

To show the of effectiveness of retention of .particle size upon dispersing zinc oxide into a oil like octyl palimtate, the following experiment was conducted;

Zinc oxide was treated using the procedure shown above. Examples 4, 10 and an untreated zinc oxide were dispersed in octyl palmitate. The higher the value of the particle size, the greater the degree of agglomeration.

| Material Tested | Particle Size | Swell* |
| --- | --- | --- |
| Example # 4 (current invention) | 203 nm | 1.00 |
| Example #10 (Non-current invention) | 486 nm | 2.39 |
| No Treatment (control) | 523 nm | 2.57 | nm is nanometer
*Swell = particle size of test zinc oxide/Particle size treated zinc oxide The effectiveness of coating the zinc oxide with the compounds of the present invention is clear. The untreated material and the zinc oxide treated with the silicone compounds which are not of the present invention both swell in the test oil.

(b) Viscosity in Formulations

The viscosity of a dispersion of zinc oxide in octyl palmitate is also an indication of the effectiveness of the treatment of zinc oxide. Particles which are effectively treated do not swell in oil. The more the zinc oxide swells the higher the viscosity of a dispersion.

The following test formula was evaluated;

| % Weight | Material |
| --- | --- |
| 33.0 | Zinc Oxide |
| 67.0 | Octyl Palmitate |
| 100.0 | |

The dispersions were made using a sonic probe 100 watts at 50% power. The viscosity was measured using a Brookfield Viscometer. Again the higher the viscosity, the greater the oil swell and the less efficient the coating.

| Example | Viscosity |
| --- | --- |
| Untreated Zinc Oxide | |
| Untreated | 1480 cps |
| Silicone Compounds of the Present Invention | |
| 12 | 321 cps |
| 16 | 315 cps |
| 18 | 256 cps |
| Silicone Compounds Not of the Present Invention (For comparison) | |
| 19 | 1260 cps |
| 22 | 1180 cps |

The effectiveness of coating the zinc oxide with the compounds of the present invention is clear. A dramatically lower viscosity results when treatment is affected using the compounds of the present invention.

(c) pH Drift

As indicated above pH in an aqueous emulsion is a good indication of the amount of reactive groups present on the zinc oxide. The following test formula was evaluated;

| % Weight | Material |
| --- | --- |
| 7.5 | Zinc Oxide |
| 42.5 | Octyl Palmitate |
| 46.0 | Water |
| 4.0 | Brij 35 |
| 100.0 | |

| Example | pH | Remarks |
| --- | --- | --- |
| Untreated Zinc Oxide | | |
| Untreated | 7.8 | high initial pH |
| Silicone Compounds of the Present Invention | | |
| 13 | 6.9 | Neutral pH |

The other consideration for reactivity is the effect of adding acid to the emulsion and observing the pH. Each formula above had added to it 0.5% HCl.

| Example | Initial pH | pH after HCl addition | pH Drop |
| --- | --- | --- | --- |
| Untreated Zinc Oxide | | | |
| Untreated | 7.8 | 6.5 | 1.3 units |
| Silicone Compounds of the Present Invention | | | |
| Example | pH | pH after HCl addition | pH Drop |
| 13 | 6.9 | 5.3 | 1.6 units |

The above data shows that the addition of HCl to the emulsion has a more dramatic pH reduction affect upon the emulsion which has the treated zinc oxide. That is the treated material has no reactive sites on the surface that would contribute to the buffering affect noted with the untreated zinc oxide. The emulsion made with the treated material dropped 0.3 more units than the untreated. The 0.3 units of pH drop is due the reactive groups on the zinc oxide consuming the acid.

The hydrophobized zinc oxide is used in a variety of applications and formulations. These applications include personal care sun screen applications. The formulations contain zinc oxide and other ingredients which may include water, inorganic pigments, organic pigments, emulsifiers, oil soluble sun screens, water soluble sun screens, alpha hydroxy acids, dispersants, oil soluble vitamins, water soluble vitamins, waxes and silicone.

We claim:

1. A process for protecting the skin from the ultra violet rays of the sun, which comprises contacting the skin with an effective protecting concentration of a hydrophobic zinc oxide which is prepared by the reaction of a silicone compound conforming to the following structure:

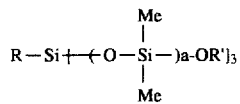

Me is methyl;

R is alkyl having one to ten carbon atoms;

R' is methyl or ethyl;

a is an integer ranging from 4 to 12;

with zinc oxide.

2. A process of claim 1 wherein said effective protecting concentration ranges between 0.1% and 25% by weight.

3. A process of claim 1 wherein said effective protecting concentration ranges between 0.5% and 20% by weight hydrophobic zinc oxide.

4. A process of claim 1 wherein said effective protecting concentration ranges between 1.0% and 10% by weight hydrophobic zinc oxide.

5. A process of claim 1 wherein a is an integer ranging from 6 to 12.

6. A process of claim 1 wherein a is an integer ranging from 4 to 8.

7. A process of claim 1 wherein R is methyl.

8. A process of claim 7 wherein said effective protecting concentration ranges between 0.1% and 25% by weight.

9. A process of claim 7 wherein said effective protecting concentration ranges between 0.5% and 20% by weight hydrophobic zinc oxide.

10. A process of claim 7 wherein said effective protecting concentration ranges between 1.0% and 10% by weight hydrophobic zinc oxide.

11. A process of claim 2 wherein R is octyl.

12. A process of claim 11 wherein said effective protecting concentration ranges between 0.1% and 25% by weight.

13. A process of claim 11 wherein said effective protecting concentration ranges between 0.5% and 20% by weight hydrophobic zinc oxide.

14. A process of claim 11 wherein said effective protecting concentration ranges between 1.0% and 10% by weight hydrophobic zinc oxide.

15. A process of claim 1 wherein R is isobutyl.

16. A process of claim 15 wherein said effective protecting concentration ranges between 0.1% and 25% by weight.

17. A process of claim 15 wherein said effective protecting concentration ranges between 0.5% and 20% by weight hydrophobic zinc oxide.

18. A process of claim 15 wherein said effective protecting concentration ranges between 1.0% and 10% by weight hydrophobic zinc oxide.

19. A process of claim 1 wherein R is ethyl.

20. A process of claim 19 wherein said effective protecting concentration ranges between 0.1% and 25% by weight.

* * * * *